(12) United States Patent
Yousef et al.

(10) Patent No.: US 12,377,058 B1
(45) Date of Patent: *Aug. 5, 2025

(54) METHOD FOR INHIBITING PROLIFERATION OF CANCER CELLS

(71) Applicant: IMAM MOHAMMAD IBN SAUD ISLAMIC UNIVERSITY, Riyadh (SA)

(72) Inventors: Tarek Ahmed Yousef, Riyadh (SA); Saad Shaaban, Riyadh (SA); Hussein Ba-Ghazal, Riyadh (SA); Marwa Sharaky, Riyadh (SA); Ahmed A. Al-Karmalawy, Riyadh (SA)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/649,785

(22) Filed: Apr. 29, 2024

(51) Int. Cl.
A61K 31/09 (2006.01)
A61P 35/00 (2006.01)
G01N 33/574 (2006.01)

(52) U.S. Cl.
CPC ............ *A61K 31/09* (2013.01); *A61P 35/00* (2018.01); *G01N 33/57484* (2013.01); *G01N 2800/52* (2013.01)

(58) Field of Classification Search
CPC ... A61K 31/09; A61P 35/00; G01N 33/57484; G01N 2800/52
See application file for complete search history.

(56) References Cited

U.S. PATENT DOCUMENTS

| 6,169,104 B1 | 1/2001 | Tusé et al. |
| 11,814,346 B1 | 11/2023 | Shabaan et al. |
| 2005/0282872 A1 | 12/2005 | Hangeland et al. |
| 2006/0258722 A1 | 11/2006 | Yasuma et al. |

OTHER PUBLICATIONS

EvitaChem, "4-(4-Methoxyphenoxy)benzaldehyde", 2024, 8 total pages.
Schäfer Andreas, et al.; "Crystal structure of 4-(4-meth-oxy-phen-oxy)benzaldehyde", Acta Crystallographica E Crystallographic Communication Dec. 6, 2015, 71(Pt 12), 7 total pages.

*Primary Examiner* — Joseph K McKane
*Assistant Examiner* — Jalisa Holmes Ferguson
(74) *Attorney, Agent, or Firm* — Oblon, McClelland, Maier & Neustadt, L.L.P.

(57) ABSTRACT

A method for inhibiting proliferation of cancer cells includes contacting the cancer cells with a cytotoxic effective amount of an anticancer compound of Formula (I);

Formula (I)

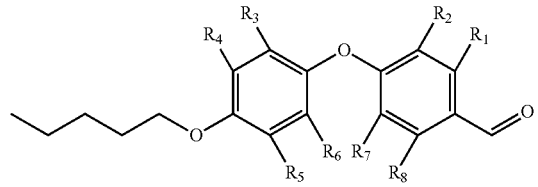

where R1 to R8 are each independently selected from a group consisting of a hydrogen atom, a halogen atom, and an optionally substituted alkyl. The anticancer compound exhibits an $IC_{50}$ of from 2 micrograms per milliliters (μg/ml) to 10 μg/ml for inhibiting the proliferation and inducing the apoptosis of cancer cells.

15 Claims, 2 Drawing Sheets

METHOD FOR INHIBITING PROLIFERATION OF CANCER CELLS

BACKGROUND

Technical Field

The present disclosure is directed toward chemical interventions for cancer proliferation and, more particularly, directed toward a method for inhibiting the proliferation of cancer cells using cytotoxic compounds.

Description of Related Art

The "background" description provided herein is to present the context of the disclosure generally. Work of the presently named inventors, to the extent it is described in this background section, as well as aspects of the description that may not otherwise qualify as prior art at the time of filing, are neither expressly nor impliedly admitted as prior art against the present invention.

Presently, cancer is a serious disease with limited clinical treatment protocols and cures. Cancer is characterized by the uncontrolled growth and spread of abnormal cells within the human body. Cancer commences when cells undergo genetic mutations that affect their normal growth, division, and death cycles. Common cancer types include but are not limited to, breast cancer, lung cancer, colorectal cancer, prostate cancer, and leukemia. Typically, apoptosis is referred to as the most effective cancer cure currently. Apoptosis, often referred to as programmed cell death or cellular suicide, is a fundamental biological process that ensures the removal of damaged, aged, or unnecessary cells, preventing the accumulation of abnormal cells such as cancer cells. Apoptosis is regulated by intrinsic pathways such as DNA damage, oxidative stress, or lack of nutrients, and extrinsic pathways such as activation of death receptors on the cell surface. Further, caspases and the Bcl-2 family are vital to the process of apoptosis. In general, caspases are protease enzymes that initiate and execute apoptosis. They cleave specific cellular proteins, leading to the dismantling of the cell. Furthermore, the Bcl-2 family regulates the intrinsic pathway by controlling the permeability of the mitochondrial membrane. Certain members promote apoptosis (pro-apoptotic), while others inhibit it (anti-apoptotic). Understanding apoptosis has led to the development of cancer therapies that induce apoptosis in malignant cells. Hence, modulating apoptosis is a target for therapeutic interventions for cancer treatment. Therefore, modulating apoptosis is a target for therapeutic interventions for cancer treatment. Additionally, cancer and inflammation are intricately linked, and various markers associated with inflammation are often implicated in cancer development and progression. Inflammatory markers may include, but are not limited to, reactive protein (CRP), interleukins (ILs), tumor necrosis factors (TNF), and reactive oxygen species (ROS). Accordingly, monitoring inflammatory markers may provide insights into the risk, progression, and treatment response of certain cancers.

However, the present methods are inefficient, detrimental to the general well-being of a cancer patient, and expensive. Thus, there arises a need for better cancer treatment protocols. Hence, it is one object of the present disclosure to provide a method for inducng aptosis in cancer cells, cytoxically treating cancer cells, killing cancer cells and/or inhibiting proliferation of cancer cells, that may circumvent the aforementioned drawbacks.

SUMMARY

In an exemplary embodiment, a method for inhibiting proliferation of cancer cells is described. The method includes contacting the cancer cells with a cytotoxic effective amount of an anticancer compound of Formula (I);

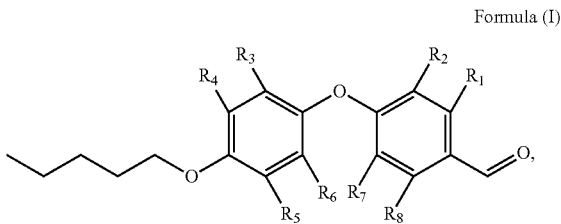

Formula (I)

where $R_1$ to $R_8$ are each independently selected from a group consisting of a hydrogen atom, a halogen atom, and an optionally substituted alkyl. The anticancer compound exhibits an $IC_{50}$ of from 2 micrograms per milliliter (μg/ml) to 10 μg/ml for inhibiting the proliferation and inducing the apoptosis of cancer cells.

In some embodiments, the anticancer compound has a Formula (II)

Formula (II)

In some embodiments, the cancer cells include one or more cancer stem cells selected from a group consisting of a breast cancer stem cell, a lung cancer stem cell, a prostate cancer stem cell, an osteosarcoma cancer stem cell, an ovarian cancer stem cell, a colon carcinoma stem cell, and a melanoma stem cell.

In some embodiments, when the cancer cells are A549 lung cancer stem cells, the method has an $IC_{50}$ of about 5-7.5 μg/ml.

In some embodiments, when the cancer cells are PC3 cancer stem cells, the method has an $IC_{50}$ of about 4-6.5 μg/ml.

In some embodiments, when the cancer cells are FaDu cancer stem cells, the method has an $IC_{50}$ of about 5-7 μg/ml.

In some embodiments, when the cancer cells are triple-MDA-MB-468 cancer stem cells, the method has an $IC_{50}$ of about 5-7 μg/ml.

In some embodiments, when the cancer cells are HeLa cancer stem cells, the method has an $IC_{50}$ of about 5.5-7 μg/ml.

In some embodiments, the method includes contacting the cancer cells with the anticancer compound of Formula (II) is in the presence of doxorubicin. In such embodiments, the method exhibits an improved inhibition efficiency at a reduced cytotoxic effective amount as compared to the use of anticancer compound in the absence of doxorubicin.

In another exemplary embodiment, a method of preparing the anticancer compound of Formula (I) is described. The method includes mixing a phenol compound, a benzaldehyde compound, and an inorganic base in a solvent to form a mixture. The preparation further includes heating the mixture at a temperature of from 120° C. to 160° C. A molar ratio of the phenol compound to the benzaldehyde compound is in a range of 1:2 to 2:1.

In some embodiments, the phenol compound is 4-pentoxyphenol.

In some embodiments, the benzaldehyde compound is 4-fluorobenzaldehyde.

In some embodiments, the inorganic base is at least one of potassium carbonate, and sodium carbonate.

In some embodiments, the solvent is dimethyl sulfoxide (DMSO).

In yet another exemplary embodiment, method of treating an individual having a disease, disorder or condition is described. The method includes screening an individual for cancer linked to one or more cancer stem cells selected from the group consisting of A549, PC3, FaDu, triple-MDA-MB-468, and HeLa. The method further includes administering to the individual, an effective amount of the anticancer compound of Formula (I) wherein the cancer is linked to the one or more cancer stem cells.

In some embodiments, the screening includes obtaining a sample from the individual and assaying the sample for the presence of the one or more cancer stem cells by measuring a baseline level of the one or more cancer stem cells in the individual.

In some embodiments, the screening further includes contacting the sample of the individual with the anticancer compound of Formula (I) and assaying cancer cell growth, proliferation and/or death, and/or expression of cancer cell markers in the sample. The screen further includes calculating the effective amount of the anticancer compound for the administering based on data obtained from the assaying.

In some embodiments, the cancer cell markers comprise one or more selected from the group consisting of a C-reactive protein (CRP), an interleukin (ILs), a tumor necrosis factor (TNF), and a reactive oxygen species (ROS).

In some embodiments, the administration of the anticancer compound is selected from a group consisting of intravenous, interperitoneal, intramuscular, and oral administration.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
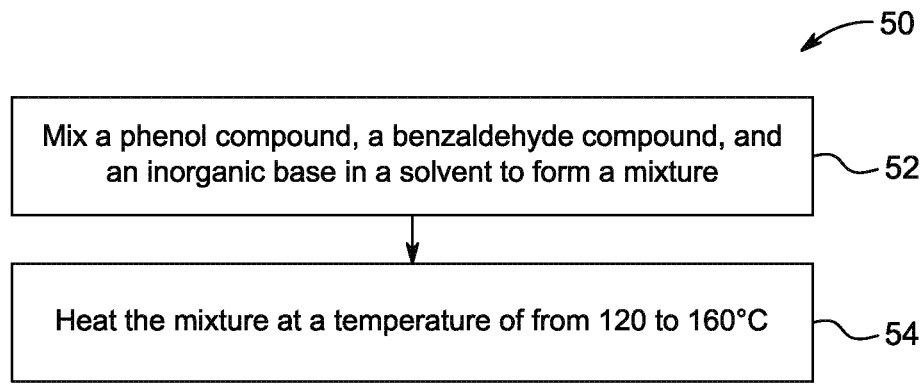
FIG. 1A is a flowchart illustrating a method for inhibiting proliferation of cancer cells, according to certain embodiments.

In the drawings, reference numerals designate identical or corresponding parts throughout the several views. Further, as used herein, the words "a," "an," and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

As used herein, the term 'cancer' refers to all types of cancer, neoplasm or malignant tumors found in mammals (e.g. humans), including leukemias, lymphomas, carcinomas, and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

An "anticancer agent" or "anticancer compound" as used herein refers to a molecule (e.g., compound, peptide, protein, nucleic acid, 0103) used to treat cancer through the destruction or inhibition of cancer cells or tissues. Anticancer agents may be selective for certain cancers or certain tissues.

"Anti-cancer agent" and "anticancer agent" or "anticancer compound" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY- 162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; hereguling; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (*Asta Medica*), A-105972 (Abbott), Hemiasterlin, 3-BAABU (Cytoskeleton/Mt. Sinai School of Medicine, i.e.

MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lso-eleutherobin A, and Z-Eleutherobin), Caribaeoside, Caribaeolin, Halichondrin B, D-64131 (*Asta Medica*), D-68144 (*Asta Medica*), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (*Asta Medica*), D-68836 (*Asta Medica*), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Gudrin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), immunotherapy (e.g., cellular immunotherapy, antibody therapy, cytokine therapy, combination immunotherapy, etc.), radioimmunotherapy (e.g., anti-CD20 monoclonal antibody conjugated to $^{111}$In, $^{90}$Y, or $^{131}$I, etc.), immune checkpoint inhibitors (e.g., CTLA4 blockade, PD-1 inhibitors, PD-L1 inhibitors, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

As used herein, the term 'halogen atom' refers to the atom of the group in the periodic table consisting of six chemically related elements: fluorine (F), chlorine (Cl), bromine (Br), or iodine (I).

As used herein, the term "substituted" refers to at least one hydrogen atom that is replaced with a non-hydrogen group, provided that normal valencies are maintained and that the substitution results in a stable compound. When a group is noted as "optionally substituted", the group may or may not contain non-hydrogen substituents. When present, the substituent(s) may be selected from alkyl, halo (e.g., chloro, bromo, iodo, fluoro), hydroxyl, alkoxy, oxo, alkanoyl, aryloxy, alkanoyloxy, amino (—NH$_2$), alkylamino (-NHalkyl), cycloalkylamino (-NHcycloalkyl), arylamino (-NHaryl), arylalkylamino (-NHarylalkyl), disubstituted amino (e.g., in which the two amino substituents are selected from alkyl, aryl or arylalkyl, including substituted variants thereof, with specific mention being made to dimethylamino), alkanoylamino, aroylamino, arylalkanoylamino, thiol, alkylthio, arylthio, arylalkylthio, alkylthiono, arylthiono, arylalkylthiono, alkylsulfonyl, arylsulfonyl, arylalkylsulfonyl, sulfonamide (e.g., —SO$_2$NH$_2$), substituted sulfonamide (e.g., —SO$_2$NHalkyl, —SO$_2$NHaryl, —SO$_2$NHarylalkyl, or cases where there are two substituents on one nitrogen selected from alkyl, aryl, or alkylalkyl), nitro, cyano, carboxy, unsubstituted amide (i.e. —CONH$_2$), substituted amide (e.g., —CONHalkyl, —CONHaryl, —CONHarylalkyl or cases where there are two substituents on one nitrogen selected from alkyl, aryl, or alkylalkyl), alkoxycarbonyl, aryl, guanidine, heterocyclyl (e.g., pyridyl, furyl, morpholinyl, pyrrolidinyl, piperazinyl, indolyl, imidazolyl, thienyl, thiazolyl, pyrrolidyl, pyrimidyl, piperidinyl, homopiperazinyl), and mixtures thereof. The substituents may themselves be optionally substituted and may be either unprotected, or protected as necessary, as known to those skilled in the art.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). In embodiments, the alkyl is fully saturated. In embodiments, the alkyl is monounsaturated. In embodiments, the alkyl is polyunsaturated. Alkyl is an uncyclized chain. Examples of saturated hydrocarbon radicals include but are not limited to, groups such as methyl, ethyl, n-propyl, isopropyl, n-butyl, t-butyl, isobutyl, sec-butyl, methyl, homologs, and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers.

As used herein, the term 'optionally substituted alkyl' refers to the alkyl group which is substituted with one, two, or three substituents independently selected from hydroxyl, alkoxy, carboxy, cyano, alkoxycarbonyl, alkylthio, alkylsulfonyl, halo, haloalkoxy, —CONRR' or —NRR' (where each R is hydrogen, alkyl, hydroxyalkyl, or alkoxyalkyl, and each R' is hydrogen, alkyl, or cycloalkyl) optionally substituted with one or two groups independently selected from alkyl, hydroxyl, alkoxy, alkylsulfonyl, halo, or —CONRR' where R and R' are as defined above.

A 'stem cell' is a cell characterized by the ability of self-renewal through mitotic cell division and the potential to differentiate into a tissue or an organ. Among mammalian stem cells, embryonic stem cells (ES cells) and somatic stem cells (e.g., HSC) can be distinguished. Embryonic stem cells reside in the blastocyst and give rise to embryonic tissues, whereas somatic stem cells reside in adult tissues for the purpose of tissue regeneration and repair. A "neural stem cell" as provided herein refers to a stem cell capable to self-renew through mitotic cell division and to differentiate into a neural cell (e.g., glia cell, neuron, astrocyte, oligodendrocyte).

As used herein, "analogue" refers to a chemical compound that is structurally similar to a parent compound, but differs slightly in composition (e.g., one atom or functional group is different, added, or removed). The analogue may or may not have different chemical or physical properties than the original compound and may or may not have improved biological and/or chemical activity. For example, the analogue may be more hydrophilic, or it may have altered reactivity as compared to the parent compound. The analogue may mimic the chemical and/or biologically active of the parent compound (i.e., it may have similar or identical activity), or, in some cases, may have increased or decreased activity. The analogue may be a naturally or non-naturally occurring variant of the original compound. Other types of analogues include isomers (enantiomers, diastereomers, and the like) and other types of chiral variants of a compound, as well as structural isomers.

As used herein, "derivative" refers to a chemically or biologically modified version of a chemical compound that is structurally similar to a parent compound and (actually or theoretically) derivable from that parent compound. A "derivative" differs from an "analogue" in that a parent compound may be the starting material to generate a "derivative," whereas the parent compound may not necessarily be used as the starting material to generate an "analogue." A derivative may or may not have different chemical or physical properties of the parent compound. For example, the derivative may be more hydrophilic, or it may have altered reactivity as compared to the parent compound. Derivatization (i.e., modification) may involve the substitution of one or more moieties within the molecule (e.g., a change in a functional group). The term "derivative" also includes conjugates, and prodrugs of a parent compound (i.e., chemically modified derivatives that can be converted into the original compound under physiological conditions).

The term "therapeutically effective amount" as used herein refers to the amount of the compound of Formula (I) is being administered which will relieve to some extent one or more of the symptoms of the disorder being treated. In reference to cancer or pathologies related to increased cell division, a therapeutically effective amount refers to that amount which has the effect of at least one of the following: (1) reducing the size of a tumor, (2) inhibiting (that is, slowing to some extent, preferably stopping) aberrant cell division, growth or proliferation, for example, cancer cell division, (3) preventing or reducing the metastasis of cancer cells, (4) relieving to some extent (or, preferably, eliminating) one or more symptoms associated with a pathology related to or caused in part by unregulated or aberrant cellular division, including for example, cancer and (5) inducing apoptosis of cancer cells or tumor cells.

As used herein, the terms "therapies" and "therapy" can refer to any method(s), composition(s), and/or agent(s), and/or compound(s) that can be used in the prevention, treatment and/or management of a cancer or one or more symptoms thereof.

As used herein, the terms "treat," "treatment," and "treating" in the context of the administration of a therapy to a subject in need thereof refer to the reduction or inhibition of the progression and or duration of cancer, the reduction or amelioration of the severity of cancer, and/or the amelioration of one or more symptoms thereof resulting from the administration of one or more therapies. In some embodiments, the subject is a mammalian subject. In one embodiment, the subject is a human. "Treating" or "treatment" of a disease includes preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer or hyperplasia, these terms simply mean that the life expectancy of an individual affected with cancer will be increased or that one or more of the symptoms of the disease will be reduced. In specific embodiments, such terms refer to one, two or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor is maintained and does not increase or increases by less than 10%, preferably less than 5%, preferably less than 4%, preferably less than 2%, and (12) an increase in the number of patients in remission. In certain embodiments, such terms refer to a stabilization or reduction in cancer stem cell population. In some embodiments, such terms refer to a stabilization or reduction in the growth of cancer cells. In some embodiments, such terms refer to stabilization or reduction in cancer stem cell population and a reduction in the cancer cell population. In some embodiments, such terms refer to a stabilization or reduction in the growth and or formation of a tumor. In some embodiments, such terms refer to the eradication, removal, or control of primary, regional, or metastatic cancer (e.g., the minimization or delay of the spread of cancer). In some embodiments, such terms refer to a reduction in mortality and/or an increase in the survival rate of a patient population. In further embodiments, such terms refer to an increase in the response rate, the durability of response, or the number of patients who respond or are in remission. In some embodiments, such terms refer to a decrease in the hospitalization rate of a patient population and/or a decrease in hospitalization length for a patient population.

The term "cytotoxically effective" is intended to qualify the amount of an agent which will achieve the goal of decreasing cancer cell count, inducing apoptosis in cancer cells and/or decreasing disease severity while avoiding adverse side effects, such as those typically associated with alternative therapies. The cytotoxically effective amount may be administered in one or more doses.

A "pharmaceutical composition" refers to a mixture of the compounds described herein or pharmaceutically acceptable salts, esters, or prodrugs thereof, with other chemical components, such as physiologically acceptable carriers and excipients.

"Pharmaceutically acceptable salt" or "pharmaceutically acceptable ester" refers to a compound in a pharmaceutically acceptable form such as an ester, a phosphate ester, a salt of an ester, or a related) which, upon administration to a subject in need thereof, provides the compound of Formula (I) described herein. Pharmaceutically acceptable salts and esters retain the biological effectiveness and properties of the free bases, which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Suitable salts include those derived from alkali metals such as potassium and sodium, and alkaline earth metals such as calcium and magnesium, among numerous other acids well-known in the art.

As used herein, a "pharmaceutically acceptable carrier" refers to a carrier or diluent that does not cause significant irritation to an organism and does not abrogate the biological activity and properties of the compound of Formula (I). the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005, which is incorporated herein by reference in its entirety. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

An "excipient" refers to an inert substance added to a pharmaceutical composition to facilitate the administration of a compound further. Examples, without limitation, of excipients include calcium carbonate, calcium phosphate, various sugars and types of starch, cellulose derivatives, gelatin, vegetable oils, and polyethylene glycols.

Unless otherwise noted, the present disclosure is intended to include all isotopes of the samples used herein.

Aspects of the present disclosure are directed towards a novel compound, 4-(4-(pentoxy)phenoxy)benzaldehyde (YS3), as potential inhibitor of non-small cell lung cancer and apoptotic inducer through p53, BAX, Caspases, BCL-2, MMP2, and MMP9 pathways. A method for inhibiting proliferation of cancer cells is described. A method for inducing apoptosis in cancer cells is described. The method includes contacting the cancer cells with a cytotoxic effective amount of an anticancer compound of Formula (I);

Formula (I)

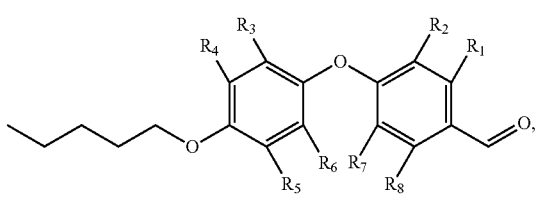

where R1 to R8 are each independently selected from a group consisting of a hydrogen atom, a halogen atom, and an optionally substituted alkyl. The anticancer compound exhibits a half maximal inhibitory concentration ($IC_{50}$) of from 2 micrograms per milliliter (μg/ml) to 10 g/ml for inhibiting the proliferation and inducing the apoptosis of cancer cells. As used herein, the term 'half maximal inhibitory concentration ($IC_{50}$)' refers to the measure of the potency of a substance in inhibiting a specific biological or biochemical function. $IC_{50}$ is a quantitative measure that indicates how much of a particular inhibitory substance (e.g., drug) is needed to inhibit, in vitro, a given biological process or biological component by 50%. The biological component can be an enzyme, cell, cell receptor, or microorganism. $IC_{50}$ values are typically expressed as molar concentration.

In some embodiments, the anticancer compound has a Formula (II)

Formula (II)

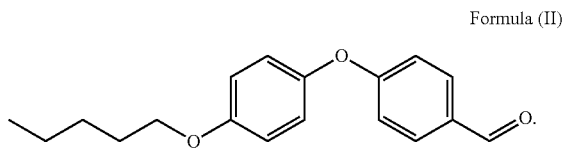 [SMILES: CCCCCOc1ccc(Oc2ccc(C=O)cc2)cc1]

In some embodiments, the cancer cells include one or more cancer stem cells selected from a group consisting of a breast cancer stem cell, a lung cancer stem cell, a prostate cancer stem cell, an osteosarcoma cancer stem cell, an ovarian cancer stem cell, a colon carcinoma stem cell, and a melanoma stem cell. In some embodiments, when the cancer cells are A549 lung cancer stem cells, the method results in an $IC_{50}$ of about 5-7.5 μg/ml with the compound of Formula (I). In some embodiments, when the cancer cells are PC3 cancer stem cells, the method has an $IC_{50}$ of about 4-6.5 μg/ml with the compound of Formula (I). In some embodiments, when the cancer cells are FaDu cancer stem cells, the method has an $IC_{50}$ of about 5-7 μg/ml with the compound of Formula (I). In some embodiments, when the cancer cells are triple-MDA-MB-468 cancer stem cells, the method has an $IC_{50}$ of about 5-7 μg/ml with the compound of Formula (I). In some embodiments, when the cancer cells are HeLa cancer stem cells, the method has an $IC_{50}$ of about 5.5-7 μg/ml with the compound of Formula (I). In some embodiments, the method includes contacting the cancer cells with the anticancer compound of Formula (II) alone or in combination with doxorubicin. When the compound of Formula (II) is contacted with the cancer cells, the method exhibits an improved inhibition efficiency at a reduced cytotoxic effective amount as compared to the use of anticancer compound in the absence of doxorubicin.

FIG. 1A illustrates a schematic flow chart of a method 50 of preparing the anticancer compound of Formula (I). The order in which the method 50 is described is not intended to be construed as a limitation, and any number of the described method steps can be combined in any order to implement the method 50. Additionally, individual steps may be removed or skipped from the method 50 without departing from the spirit and scope of the present disclosure.

At step 52, the method 50 includes mixing a phenol compound, a benzaldehyde compound, and an inorganic base in a solvent to form a mixture. As used herein, the term 'phenol' (also known as carbolic acid, phenolic acid, or benzenol) refers to an aromatic organic compound with the molecular Formula $C_6H_5OH$. In some embodiments, the phenol may include, but are not limited to, catechol (1,2-dihydroxybenzene), resorcinol (1,3-dihydroxybenzene), and hydroquinone (1,4-dihydroxybenzene). In some embodiments, the phenol compound is 4-butoxyphenol. As used herein, the term 'benzaldehyde' refers to an organic compound consisting of a benzene ring with a formyl substituent. In some embodiments, the benzaldehyde compound is 4-fluorobenzaldehyde. The base selected from the group consisting of an alkaline earth metal hydroxide such as beryllium hydroxide ($Be(OH)_2$), magnesium hydroxide ($Mg(OH)_2$), strontium hydroxide ($Sr(OH)_2$), and calcium hydroxide ($Ca(OH)_2$) and an alkali metal hydroxide such as lithium hydroxide (LiOH), sodium hydroxide (NaOH), potassium hydroxide (KOH) and rubidium hydroxide (RbOH), and cesium hydroxide (CsOH). In some embodiments, the inorganic base is at least one of potassium carbonate, and sodium carbonate. In some embodiments, the solvent may include, but is not limited to, tetrahydrofuran, ethyl acetate, dimethylformamide, acetonitrile, acetone, dimethyl sulfoxide (DMSO), nitromethane, propylene carbonate, ethanol, formic acid, n-butanol, methanol, or any combination thereof. In some embodiments, the solvent may include benzene, cyclohexane, ethanol, methanol, acetone, ethyl acetate, dichloromethane, toluene, and diethyl ether. In some embodiments, the solvent is dimethyl sulfoxide DMSO.

At step 54, the method 50 includes heating the mixture at a temperature of from 120° C. to 160° C., more preferably 135 to 145° C., and more preferably 140° C. A molar ratio of the phenol compound to the benzaldehyde compound is in a range of 1:2 to 2:1, more preferably 1:1. In some embodiments, the heating can be performed by using heating appliances such as ovens, microwaves, autoclaves, hot plates, heating mantles and tapes, oil baths, salt baths, sand baths, air baths, hot-tube furnaces, and hot-air guns.

Figure 1B:
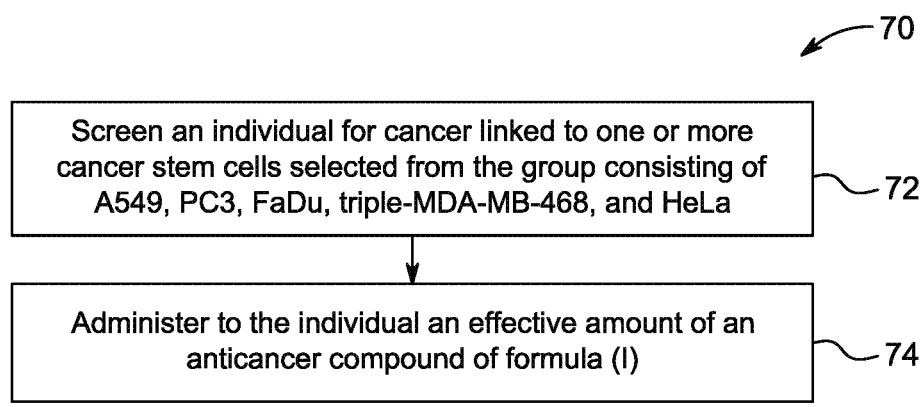
FIG. 1B is a flowchart illustrating a method of treating an individual having a disease, disorder or condition, according to certain embodiments.

FIG. 1B illustrates a schematic flow chart of a method 70 of treating an individual having a disease, disorder or condition is described. The terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. The order in which the method 70 is described is not intended to be construed as a limitation, and any number of the described method steps can be combined in any order to implement the method 70. Additionally, individual steps may be removed or skipped from the method 70 without departing from the spirit and scope of the present disclosure.

At step 72, the method 70 includes screening an individual for cancer linked to one or more cancer stem cells selected from the group consisting of non-small cell lung cancer (A549), prostate cancer (PC3), pharynx squamous carcinoma (FaDu), triple-negative breast cancer (MDA-MB-468), and cervical cancer (HeLa). In some embodiments, the screening includes obtaining a sample, such as a urine sample, plasma sample, blood sample, stool sample, tissue sample, etc., from the individual and further assaying the sample for the presence of one or more cancer stem cells by measuring a baseline level of one or more cancer stem cells in the individual. After assaying, in some embodiments, the effective amount of the anticancer compound to be administered is calculated based on the data obtained from the assay. Accordingly, the sample of the individual may be contacted with the anticancer compound of Formula (I) or Formula (II). After contacting the sample with the anticancer compound of Formula (I) or Formula (II), the sample may be again assayed for cancer cell growth, proliferation and/or death, and/or expression of cancer cell markers in the sample. In some embodiments, the cancer cell markers include one or more selected from the group consisting of a C-reactive protein (CRP), an interleukin (ILs), a tumor necrosis factor (TNF), and a reactive oxygen species (ROS).

At step 74, the method 70 includes administering to the individual an effective amount of the anticancer compound of Formula (I). The cancer is linked to one or more cancer stem cells. As used herein, the term 'administering' means oral administration, administration as a suppository, topical contact, intravenous, parenteral, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent. In some embodiments, the administration of the anticancer compound is selected from a group consisting of intravenous, interperitoneal, intramuscular, and oral administration.

In other embodiments of the present disclosure cancer cells are contacted with an amount of the compound of Formula (I) to induce apoptosis in the cancer cells and/or kill the cancer cells. The cancer cells may be treated in vitro or outside a human patient.

A pharmaceutical composition including the compound of Formula (I) of the present disclosure can then be administered orally, systemically, parenterally, by inhalation spray, rectally, or topically in dosage unit formulations containing conventional non-toxic pharmaceutically acceptable carriers, adjuvants, and vehicles as desired. In some embodiments, the method of administration of the steroid or an analogue or derivative thereof is oral. In other embodiments, the compound or an analogue or derivative thereof is administered by injection, such as, for example, through a peritumoral injection.

Topical administration can also involve the use of transdermal administration, such as transdermal patches or iontophoresis devices. The term parenteral, as used herein, includes intravesical, intradermal, transdermal, subcutaneous, intramuscular, intralesional, intracranial, intrapulmonary, intracardial, intrasternal, and sublingual injections, or infusion techniques. Formulation of drugs is discussed in, for example, Hoover, John E., Remington's Pharmaceutical Sciences, Mack Publishing Co., Easton, Pa.; 1975. Another example includes Liberman, H. A. and Lachman, L., Eds., Pharmaceutical Dosage Forms, Marcel Decker, New York, N.Y., 1980, which is incorporated herein by reference in its entirety.

Injectable preparations, for example, sterile injectable aqueous or oleaginous suspensions, can be Formulated according to the known art using suitable dispersing or wetting agents and suspending agents. The sterile injectable preparation can also be a sterile injectable solution or suspension in a nontoxic, parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, any fixed oil can be employed, including synthetic mono- or diglycerides. In addition, fatty acids such as oleic acid find use in the preparation of injectables. Dimethyl acetamide, surfactants including ionic and nonionic detergents, and polyethylene glycols can be used. Mixtures of solvents and wetting agents, such as those discussed above, are also useful. Suppositories for rectal administration of the compound or an analogue or derivative thereof can be prepared by mixing the steroid or an analogue or derivative thereof with a suitable non-irritating excipient such as cocoa butter, synthetic mono- di- or triglycerides, fatty acids, and polyethylene glycols that are solid at ordinary temperatures but liquid at the rectal temperature and will therefore melt in the rectum and release the drug.

Solid dosage forms for oral administration can include capsules, tablets, pills, powders, and granules. In such solid dosage forms, the compounds of this disclosure are ordinarily combined with one or more adjuvants appropriate to the indicated route of administration. If administered per os, a contemplated steroid or an analogue or derivative thereof can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in a dispersion of the active compound in hydroxypropyl methylcellulose. In the case of capsules, tablets, and pills, the dosage forms can also comprise buffering agents such as sodium citrate, magnesium or calcium carbonate, or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A contemplated steroid or an analogue or derivative thereof of the present disclosure can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending, agents, and sweetening, flavouring, and perfuming agents.

The amount of compound of Formula (I) that can be combined with the carrier materials to produce a single dosage form varies depending upon the mammalian subject treated and the particular mode of administration.

Cancers such as but not limited to sarcomas, carcinomas, melanomas, myelomas, gliomas, and lymphomas can be treated or prevented with the compound of Formula (I) provided herein. In some embodiments, a pharmaceutical composition incorporating the compound of Formula (I) of the present disclosure is present in an amount effective for treating a patient having a proliferative disorder selected from the group consisting of head and neck cancer, breast cancer, lung cancer, colon cancer, prostate cancer, gliomas, glioblastoma, astrocytomas, glioblastoma multiforme, Bannayan-Zonana syndrome, Cowden disease, Lhermitte-Duclos disease, inflammatory breast cancer, Wilm's tumor, Ewing's sarcoma, Rhabdomyosarcoma, ependymoma, medulloblastoma, kidney cancer, liver cancer, melanoma, pancreatic cancer, sarcoma, osteosarcoma, giant cell tumor of bone, thyroid cancer, lymphoblastic T cell leukemia, Chronic myelogenous leukemia, Chronic lymphocytic leukemia, Hairy-cell leukemia, acute lymphoblastic leukemia, acute myelogenous leukemia, AML, Chronic neutrophilic leukemia, Acute lymphoblastic T cell leukemia, plasmacytoma, Immunoblastic large cell leukemia, Mantle cell leukemia, Multiple myeloma Megakaryoblastic leukemia, multiple myeloma, acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), testicular cancer, and the like.

The methods for treating cancer and other proliferative disorders described herein inhibit, remove, eradicate, reduce, regress, diminish, arrest, or stabilize a cancerous tumor, including at least one of the tumor growth, tumor cell viability, tumor cell division, and proliferation, tumor metabolism, blood flow to the tumor and metastasis of the tumor. In some embodiments, after treatment with the compound of Formula (I) or a pharmaceutical composition thereof, the size of a tumor, whether by volume, weight, or diameter, is reduced by at least 5%, 10%, 15%, 20%, 25%, 30%, 40%, 50%, 60%, 70%, 75%, relative to the tumor size before treatment. In other embodiments, after treatment with the compound of Formula (I) or a pharmaceutical composition thereof, the size of a tumor does not reduce but is maintained the same as the tumor size before treatment. Methods of assessing tumor size include but are not limited to CT scan, MRI, DCE-MRI, and PET Scan.

The dosage and treatment duration are dependent on factors such as the bioavailability of a drug, administration mode, toxicity of a drug, gender, age, lifestyle, body weight, the use of other drugs and dietary supplements, cancer stage, tolerance, and resistance of the body to the administered drug, etc., then determined and adjusted accordingly. The compound of Formula (I) or a pharmaceutical composition thereof may be administered in a single dose or multiple individual divided doses. In some embodiments, the interval of time between the administration of the compound of Formula (I) or Formula (II) or a pharmaceutical composition thereof and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks. 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period in between. In certain embodiments, the compound of Formula (I) or Formula (II) and one or more additional therapies are administered less than 1 day, 1 week, 2 weeks, 3 weeks, 4 weeks, one month, 2 months, 3 months, 6 months, 1 year, 2 years, or 5 years apart.

In certain embodiments, the compound of Formula (I) of the present disclosure or a pharmaceutical composition thereof may be used in combination with one or more other antineoplastic or chemotherapeutic agents. A non-limiting list of examples of chemotherapeutic agents are aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosamide, irinotecan, lomustine, mechelorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cis-platin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguaniue), tipifarnib. Examples of antineoplastic agents which are protein kinase inhibitors include imatinib, erlotinib, sorafenib, sunitinib, dasatinib, nilotinib, lapatinib, gefitinib, temsirolimus, everolimus, rapamycin, bosutinib, pazopanib, axitinib, neratinib, vatalanib, pazopanib, midostaurin, and enzastaurin. Examples for antineoplastic agents which are antibodies comprise trastuzumab, cetuximab, panitumumab, rituximab, bevacizumab, mapatumumab, conatumumab, lexatumumab and the like.

EXAMPLES

The following examples demonstrate a method for inhibiting proliferation of cancer cells, a method for inducing apoptosis in cancer cells, and/or a method of cytotoxically treating cancer cells using the compound of present disclosure. The examples are provided solely for illustration and are not to be construed as limitations of the present disclosure, as many variations thereof are possible without departing from the spirit and scope of the present disclosure.

Example 1: Synthesis of
4-(4-(pentoxy)phenoxy)benzaldehyde (YS3)

Figure 2:
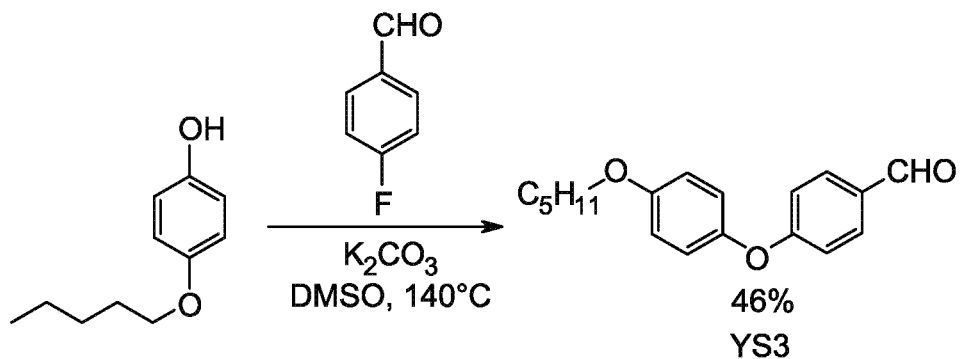
FIG. 2 is a schematic illustration depicting synthesis of 4-(4-(pentoxy)phenoxy)benzaldehyde (YS3), according to certain embodiments.

Referring to FIG. 2, synthesis of 4-(4-(pentoxy)phenoxy) benzaldehyde (YS3) is illustrated, according to certain embodiments. 2 millimoles (mmol) of phenol (1) was dissolved in 2 milliliters of dimethyl sulfoxide (DMSO). Further, potassium carbonate (4 mmol), and p-fluorobenzaldehyde (2 mmol) were added to the above-mentioned mixture of phenol and DMSO. The mixture was heated in an oil bath at 140 degrees Celsius (° C.) for 3 hours. A resultant mixture was poured into ice after completion, to give product YS3 in 46% yield.

Compound YS3 was synthesized from the reaction of 4-(pentyloxy)phenol (1) (2 mmol), potassium carbonate (4 mmol), and p-fluorobenzaldehyde (2 mmol). YS3 was isolated as a white powder; m.p. 50-51° C.; Yield: (46%); FT-IR (v, cm-1): 2933 (C—H, stretching), 1694 (—CHO), 1232, 1210, 1016. 1H-NMR (CDCl$_3$, 400 MHz): δ 0.87-0.91 (t, 3H, CH$_3$), 1.29-1.37 (m, 6H, 3xCH$_2$), 1.40-1.48 (m, 2H, CH$_2$), 3.87-3.97 (t, 2H, —O—CH$_2$), 6.87-6.93 (m, 5H, Ar—H) 7.44-7.47 (d, 2H, Ar—H, J=12 Hz), 7.73-7.76 (dd, H, Ar—H, J=12 Hz), 9.93 (s, 1H, CHO) ppm; 13C-NMR (CDCl$_3$, 100 MHz): δ 190.71 (CHO), 164.16 (C, Ar—C), 156.45 (C, Ar—C), 147.98 (C, Ar—C), 131.90 (2xCH, Ar—C), 130.85 (C, Ar—C), 121.75 (2xCH, Ar—C), 116.75 (2xCH, Ar—C), 115.73 (2xCH, Ar—C), 68.51 (0-CH$_2$), 31.76 (CH$_2$), 29.28 (CH$_2$), 22.59 (CH$_2$), 14.05 (CH$_3$) ppm. MS (m/z, %): 265.4 (100%), 284.4 (M+, 22.41), 309.4 (M++Na+2, 54.23). Calculated for C$_{18}$H$_{20}$O$_3$ (284.14): C, 76.03; H, 7.09. Found: C, 76.10; H, 7.12.

Based on their different spectrum data, the structure of YS3 compound was determined. The infrared (IR) spectra of compound YS3 exhibited the characteristic absorption band of (—CHO) at 1694 cm$^{-1}$, absorption band at 2933 cm$^{-1}$ related to (C—H, stretching). $^1$H nuclear magnetic resonance spectroscopy (NMR) spectra of compound YS3 showed a singlet signal at δ9.93 ppm assigned to the protons of (—CHO) group. As well as two-triplet signals at δ0.87-0.91 ppm and δ3.87-3.97 ppm corresponding to the protons of (CH$_3$) and (—O—CH$_2$), respectively. The aromatic signals appear at δ7.76-6.78 ppm. Further, $^{13}$C NMR for compound YS3 established a signal at 6190.71 ppm representatives for the carbonyl groups. Four carbon signals at δ68.51 ppm, δ31.76 ppm, δ29.28 ppm, and δ22.59 ppm due to the four methylene groups. MS (m/z, %): 265.4 (100%), 284.4 (M+, 22.41), 309.4 (M++Na+2, 54.23). Calcd. for C18H20O3 (284.14): C, 76.03; H, 7.09. Found: C, 76.10; H, 7.12.

Example 2: Results

Figure 3:
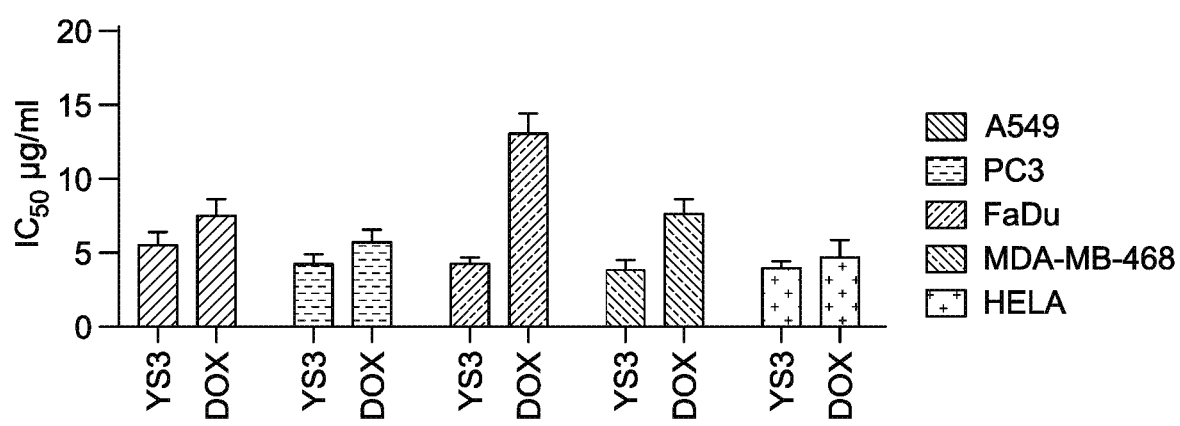
FIG. 3 is a graph depicting growth inhibition percentage of YS3 against a plurality of cancer cells, according to certain embodiments.

Referring to FIG. 3, cytotoxic inhibitory concentration of 50 (IC$_{50}$) evaluation of YS3 against various cancer cells is illustrated. As can be seen from FIG. 3, YS3 has an IC$_{50}$ of about 5 µg/ml against A549 lung cancer stem cells, an IC$_{50}$ of about 4 µg/ml against PC3 cancer stem cells, an IC$_{50}$ of about 4 µg/ml against FaDu cancer stem cells. Further, YS3 has an IC$_{50}$ of about 4.5 µg/ml against MDA-MB-468 cancer stem cells and an IC$_{50}$ of about 5 µg/ml against HELA cancer stem cells. The performance of YS3 was compared to commercially available doxorubicin (DOX), and the results indicate that the performance of YS3 is comparable to DOX in some cell lines (A549, PC3, and HeLa).

Aspects of the present disclosure include a method for inhibiting the proliferation of cancer cells in the human body and a method for inducing apoptosis in cancer cells to cytotoxically treat cancer cells. Further, the compound YS3, as used in the present disclosure, produced favorable results against a plurality of cancer stem cells in clinical laboratory settings.

Numerous modifications and variations of the present disclosure are possible in light of the above teachings. It is therefore to be understood that within the scope of the appended claims, the invention may be practiced otherwise than as specifically described herein.

The invention claimed is:

1. A method for inhibiting proliferation of cancer cells, comprising:
contacting the cancer cells with a cytotoxic effective amount of an anticancer compound of Formula (I);

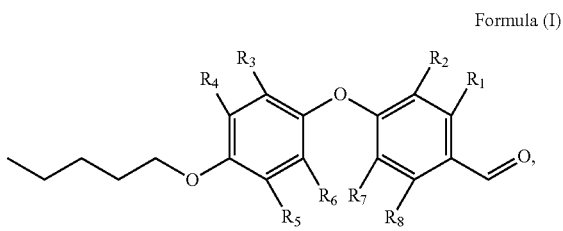

Formula (I)

wherein $R_1$ to $R_8$ are each independently selected from a group consisting of a hydrogen atom, a halogen atom, and an optionally substituted alkyl; and wherein the anticancer compound exhibits an $IC_{50}$ of from 2 to 10 µg/ml for inhibiting the proliferation and inducing the apoptosis of cancer cells.

2. The method of claim 1, wherein the anticancer compound has a Formula (II)

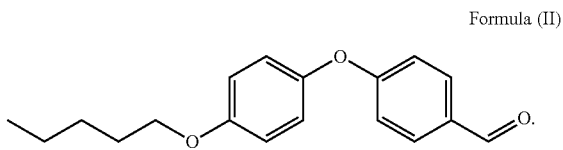 [SMILES: CCCCCOc1ccc(Oc2ccc(C=O)cc2)cc1]

Formula (II)

3. The method of claim 1, wherein the cancer cells comprise one or more cancer stem cells selected from a group consisting of a breast cancer stem cell, a lung cancer stem cell, a prostate cancer stem cell, an osteosarcoma cancer stem cell, an ovarian cancer stem cell, a colon carcinoma stem cell, and a melanoma stem cell.

4. The method of claim 1, wherein the cancer cells are A549 lung cancer stem cells, and wherein the method has an $IC_{50}$ of about 5-7.5 µg/ml.

5. The method of claim 1, wherein the cancer cells are PC3 cancer stem cells, and wherein the method has an $IC_{50}$ of about 4-6.5 µg/ml.

6. The method of claim 1, wherein the cancer cells are FaDu cancer stem cells, and wherein the method has an $IC_{50}$ of about 5-7 µg/ml.

7. The method of claim 1, wherein the cancer cells are triple-MDA-MB-468 cancer stem cells, and wherein the method has an $IC_{50}$ of about 5-7 µg/ml.

8. The method of claim 1, wherein the cancer cells are HeLa cancer stem cells, and wherein the method has an $IC_{50}$ of about 5.5-7 µg/ml.

9. The method of claim 2, wherein the contacting the cancer cells with the anticancer compound of Formula (II) is in the presence of doxorubicin, and wherein the method exhibits an improved inhibition efficiency at a reduced cytotoxic effective amount as compared to the use of anticancer compound in the absence of doxorubicin.

10. The method of claim 1, further comprising preparing the anticancer compound of Formula (I) by:
mixing a phenol compound, a benzaldehyde compound, and an inorganic base in a solvent to form a mixture; and
heating the mixture at a temperature of from 120 to 160° C.;
wherein a molar ratio of the phenol compound to the benzaldehyde compound is in a range of 1:2 to 2:1.

11. The method of claim 10, wherein the phenol compound is 4-pentoxyphenol.

12. The method of claim 10, wherein the benzaldehyde compound is 4-fluorobenzaldehyde.

13. The method of claim 10, wherein the inorganic base is at least one of potassium carbonate, and sodium carbonate.

14. The method of claim 10, wherein the solvent is dimethyl sulfoxide (DMSO).

15. The method of claim 10, wherein a molar ratio of the phenol compound to the inorganic base is in a range of 1:1 to 1:2, and wherein a molar ratio of the benzaldehyde compound to the inorganic base is in a range of 1:1 to 1:2.

* * * * *